United States Patent [19]

Baillie

[11] Patent Number: 4,952,374
[45] Date of Patent: Aug. 28, 1990

[54] ROTATING CATALYST BED WITH PRESSURIZED GAS SEAL FOR METHANE CONVERSION SYSTEM

[75] Inventor: Lloyd A. Baillie, Plano, Tex.

[73] Assignee: Atlantic Richfield Company, Los Angeles, Calif.

[21] Appl. No.: 876,325

[22] Filed: Jun. 19, 1986

[51] Int. Cl.⁵ .................... G05D 11/00; G05D 16/20
[52] U.S. Cl. ................................. 422/110; 422/112; 422/209; 422/211; 422/223; 422/236; 422/237
[58] Field of Search ............... 422/209, 236, 239, 112, 422/110, 211, 223

[56] References Cited

U.S. PATENT DOCUMENTS

| | | | |
|---|---|---|---|
| 2,246,345 | 6/1941 | Campbell | 422/209 |
| 3,885,917 | 5/1975 | Osenkina et al. | 422/145 |
| 4,173,527 | 11/1979 | Heffley et al. | 422/145 |
| 4,664,813 | 5/1987 | Schneider | 34/242 |

Primary Examiner—Robert J. Warden
Assistant Examiner—Timothy M. McMahon
Attorney, Agent, or Firm—Michael E. Martin

[57] ABSTRACT

Hydrocarbon gas, such as methane, is partially oxidized by flowing the gas through a moving catalyst bed supported on a rotating drum disposed in a partitioned duct. Catalyst is regenerated by exposure to an oxygen containing gas flowing through a passage formed in the duct. A gas seal is formed between the duct partition and a surface of the catalyst support drum on the downstream side of the drum to minimize the leakage flow of hydrocarbon gas into the regenerator gas. The pressures of the hydrocarbon gas and regenerator gas are regulated upstream of the catalyst bed to minimize leakage flow of one gas into the flow space of the other gas through a space formed between the duct partition and the drum upstream of the catalyst bed.

3 Claims, 2 Drawing Sheets

ROTATING CATALYST BED WITH PRESSURIZED GAS SEAL FOR METHANE CONVERSION SYSTEM

BACKGROUND OF THE INVENTION

1. Field of the Invention

The present invention pertains to an apparatus for converting methane to a liquid hydrocarbon by partial oxidation using a catalyst disposed in a rotating bed which provides for oxidizing and reducing the catalyst.

2. Background

Certain hydrocarbons, such as methane, occur in gaseous form in large deposits in somewhat remote regions of the world. The transportation of hydrocarbons, such as methane, in gaseous form is relatively inefficient, hence it is desirable to convert such gases to a readily condensable hydrocarbon for ease of transportation or for other process reasons.

The partial oxidation of methane and certain other hydrocarbon gases can produce substances which are easier to handle and transport in liquid form or are more useful for producing certain chemical reactions. Several processes have been considered for the conversion of methane to other hydrocarbon products and one process involves the use of manganese oxide as a catalyst. A preferred process involves heating an oxygen containing gas, such as ambient air, to a relatively high temperature for conditioning or regenerating the catalyst and then exposing the regenerated catalyst to a flowstream of methane gas to carry out the conversion process.

In accordance with the present invention, a particularly desirable way of handling the catalyst in carrying out the conversion process has been deemed to include the utilization of a rotary catalyst bed support structure so that a moving bed of catalyst material is alternately exposed to the methane or other hydrocarbon gas flowstream and then to a catalyst regeneration gas flowstream, such as heated air. In order to have the conversion reaction take place at a stable and desired condition, the hydrocarbon gas flowstream and the regenerator gas flowstream are maintained at particular pressure and temperature conditions entering the moving bed apparatus. However, the properties of the respective gases result in unequal friction pressure losses as the gas flowstreams pass through the catalyst bed, thereby complicating the process of sealing the moving bed from gas leakage of one gas into the flow path of the other gas.

The present invention is directed to an improved apparatus for overcoming some of the problems inherent in developing an efficient and attractive process for converting methane or other gaseous hydrocarbons utilizing a moving catalyst bed.

SUMMARY OF THE INVENTION

The present invention provides an improved apparatus for conversion of a hydrocarbon gas comprising providing a moving catalyst bed which is disposed in a rotating support structure and wherein predetermined pressure conditions of the hydrocarbon gas and a catalyst regenerator gas are maintained during flow of the gases through the catalyst bed by way of separate flow passages. In accordance with one important aspect of the present invention, a conversion apparatus is provided comprising a rotating catalyst bed support structure characterized by a generally cylindrical drum supporting a bed of catalyst material which is alternately exposed to an oxygen containing atmosphere for regenerating the catalyst and to the gaseous flowstream to be converted for at least partially oxidizing the hydrocarbon gas. The rotating catalyst bed and its support structure are interposed in means comprising a partitioned duct which provides separate hydrocarbon gas and catalyst regenerator gas flowstreams.

In accordance with another important aspect of the invention, the respective gas flowstreams are maintained at predetermined pressures approaching the catalyst bed. Under conditions wherein the gaseous flowstreams undergo pressure losses as the respective flowstreams pass through the catalyst bed, a unique pressurized gas seal arrangement is provided for minimizing the flow of hydrocarbon gas into the regenerator gas flowstream.

The present invention further provides a hydrocarbon gas conversion system having a moving catalyst bed, and means forming a partitioned duct for conducting flowstreams of hydrocarbon gases and catalyst regenerator gases through the catalyst bed at substantially equal pressure conditions upstream of the catalyst bed, which pressure conditions are maintained by a suitable pressure controller. A pressurized gas seal is provided on the downstream side of the bed support structure at the partition and is controlled to maintain a seal gas pressure such as to minimize the leakage of hydrocarbon gases into the regenerator gas flowstream.

Those skilled in the art will further appreciate the abovenoted features and advantages of the present invention, together with other superior aspects thereof, upon reading the detailed description which follows in conjunction with the drawing.

DESCRIPTION OF PREFERRED EMBODIMENTS

Figure 1:
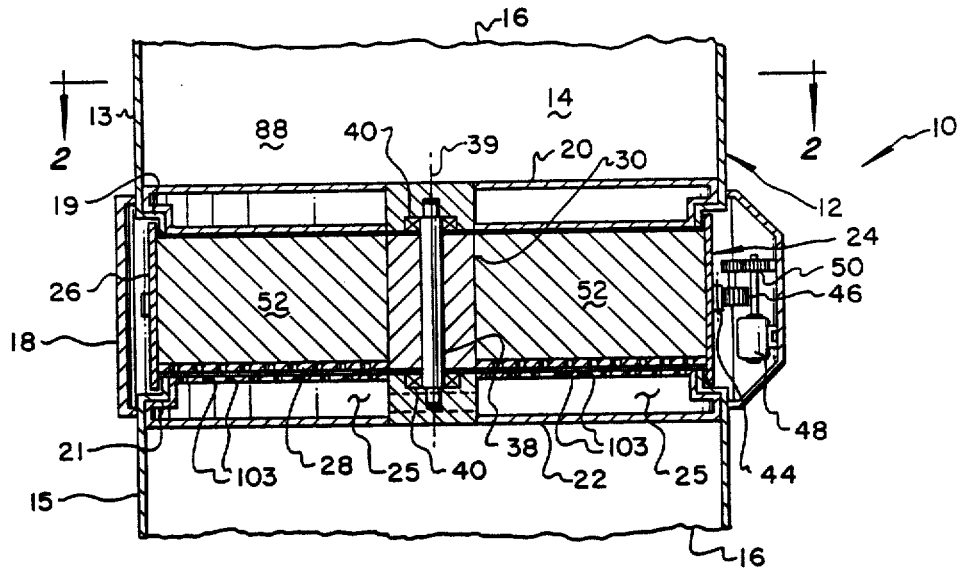
FIG. 1 is a vertical, central section view taken along line 1—1 of FIG. 2 and showing a portion of a moving catalyst bed apparatus in accordance with the present invention.

In the description which follows, like parts are marked throughout the specification and drawing with the same reference numerals, respectively. The drawing figures are in somewhat schematic form in the interest of clarity and conciseness. Conventional elements are shown schematically and may be referred to in general terms only throughout the specification.

The system or apparatus of the present invention contemplates the conversion of a hydrocarbon gas such as methane, utilizing an oxidative synthesizing agent comprising a metal oxide compound which is supported on a unique structure. In accordance with one embodiment of the present invention, methane gas is converted to a higher composition ($C_{2+}$) hydrocarbon product and co-product water by reducing a metal oxide such as manganese oxide at a temperature within the range of about 500° C. to 1000° C. The manganese oxide is supported on catalyst support material such as a relatively porous silicon oxide or aluminum oxide composition. In particular, the catalyst or synthesizing agent support comprises aluminum oxide pellets or cylinders having nominal dimensions of about 0.375 inches in length by about 0.125 inches diameter. Such a catalyst or synthesizing agent is available commercially under the trademark EMCAT 100.

Figure 2:
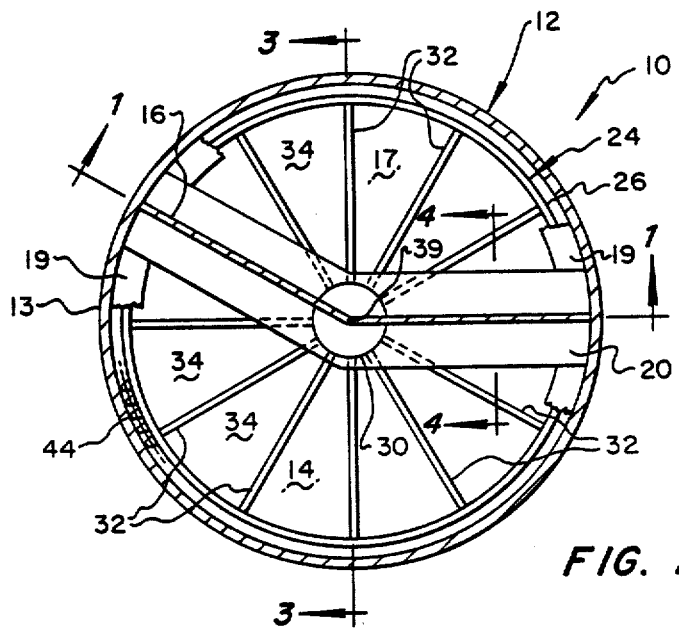
FIG. 2 is a view taken generally along the line 2—2 of FIG. 1.

Referring to FIG. 1, there is illustrated in somewhat schematic form one embodiment of an improved catalyst support apparatus for continuously exposing the oxidative synthesizing or catalyst substance to the hydrocarbon gas to "reduce" a metal oxide catalyst and convert the hydrocarbon gas to a higher composition hydrocarbon and then regenerate the reduced metal oxide catalyst by contacting the catalyst material with an oxygen containing gas, such as air, preferably at elevated temperatures. In FIGS. 1 and 2, the improved apparatus is generally designated by the numeral 10 and is characterized by a partitioned duct 12 having a first interior space or flow passage 14 and a partition 16. The duct 12 may be of rectangular or cylindrical cross-sectional configuration, the latter being shown, and may be formed in essentially two sections 13 and 15 which are interconnected by an intermediate housing 18. The duct sections 13 and 15 each include re-entrant annular rim portions 19 and 21, FIG. 1. As shown in FIG. 2, part of the rim portion 19 is broken away to illustrate the construction of a below described drum member. The duct 12 also includes suitable transverse support members 20 and 22 which are configured to support a rotatable, generally cylindrical drum member 24. The drum 24 includes an outer cylindrical wall 26, a foraminous bottom plate or screen 28 and a central hub 30.

As shown in FIG. 2, the drum 24 is preferably strengthened by a plurality of radially extending divider plates 32 which, together with the wall 26 and bottom plate 28, form a plurality of somewhat wedge or circular sector shaped chambers 34. The hub 30 is supported by a central support shaft 38 which is journaled in suitable bearings 40 supported by the respective support members 20 and 22 for rotation about a generally vertical axis 39. The drum 24 may be rotated by one of several suitable drive means, including providing the outer wall 26 with a ring gear 44 which is meshed with a drive pinion 46 drivably connected to a suitable motor 48 through a gear reduction drive train 50.

Figure 4:
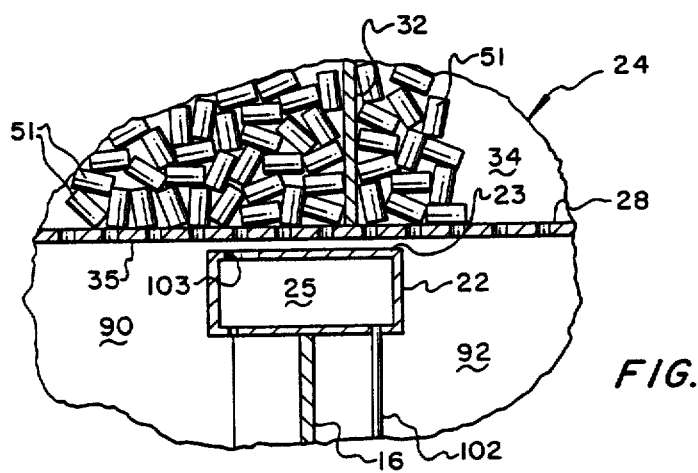
FIG. 4 is a detail section view taken along line 4—4 of FIG. 2 showing one of the gas seals.

The chambers 34 are preferably filled with the aforementioned oxidative synthesizing agent in the form of support pellets or cylinders 51, see FIG. 4 also, described above to form a catalyst bed 52 in each of the chambers 34. By continuously rotating the drum 24 between the passage or space 14 and a passage or space 17, see FIGS. 2 and 3, and separated from the space 14 by the partition 16, the catalyst beds 52 may be alternately regenerated by being exposed to an oxygen containing gas flowing through the space 14 and then reduced to partially oxidize a hydrocarbon gas, such as methane, flowing through the space 17. The unequal cross-sectional areas provided by the spaces 14 and 17 and as defined by the partition 16 are based on the total bed area which must be exposed to an oxygen containing gas, such as air, in the space 14 and to a hydrocarbon gas, such as methane, in the space 17 for an example to be given in detail hereinbelow.

Figure 3:
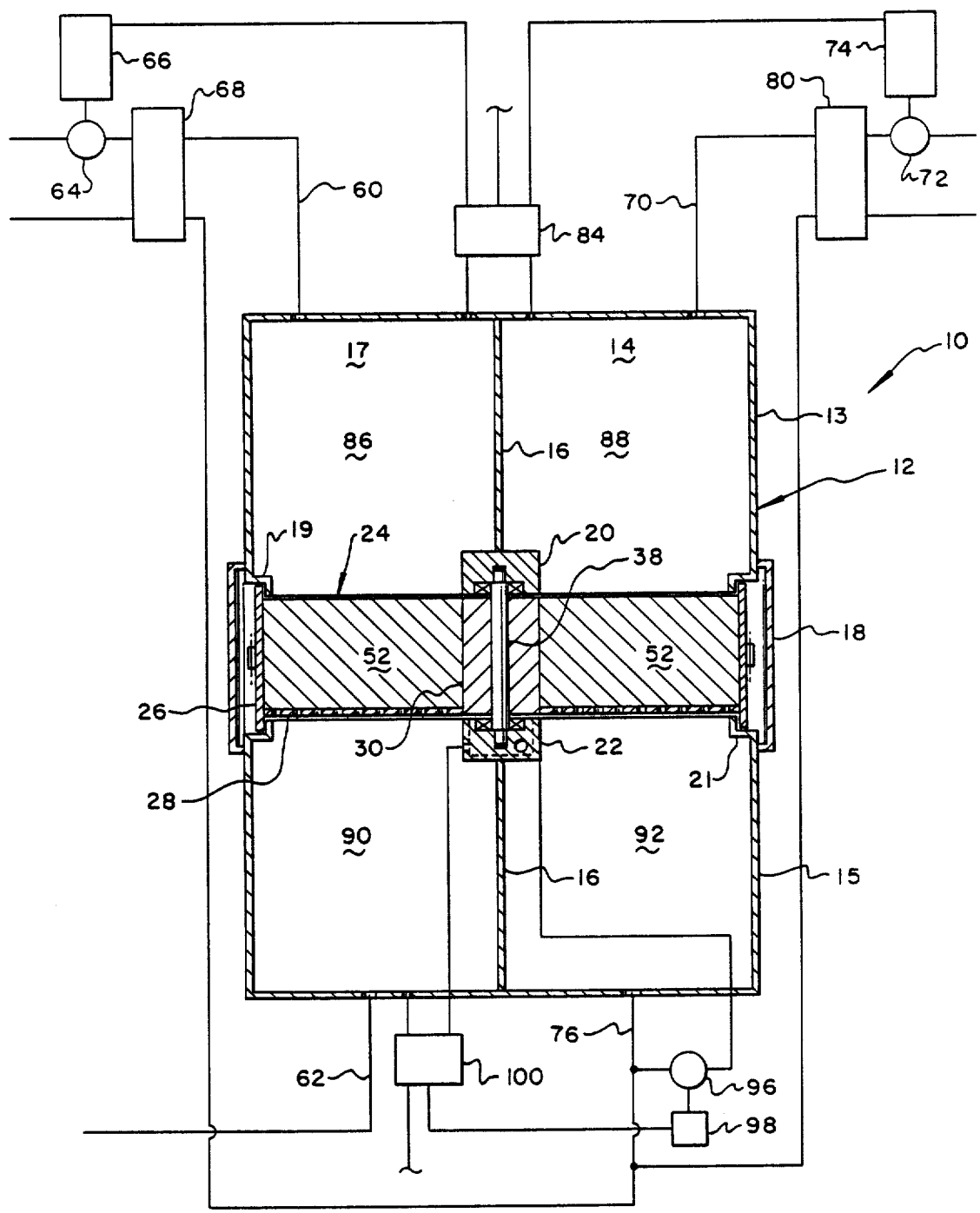
FIG. 3 is a schematic diagram of a gas conversion system, including a somewhat schematic section view of the moving catalyst bed apparatus taken along line 3—3 of FIG. 2.

Referring to FIG. 3, the apparatus 10 is adapted to be interposed in a system for converting a hydrocarbon gas to a higher hydrocarbon composition by rotating the drum 24 continuously while pumping a hydrocarbon gas, such as methane, through a conduit 60 in communication with the space 17, through the drum chambers 34 and the bottom plate or screen 28 and from the duct 12 by way of a conduit 62. The converted hydrocarbon gas may then be further treated in accordance with processes which are not part of the present invention. Hydrocarbon gas is supplied through the conduit 60 by a pump 64 driven by suitable motor means 66. The hydrocarbon gas may be passed through a heat exchanger, generally designated by the numeral 68, which may be of a type not completely unlike the apparatus 10 and similar in some respects to a device known as an air preheater made under the trademark Ljungstrom by Combustion Engineering Company of Wellsville, N.Y.

The duct 12 is also supplied with an oxygen containing gas, such as preheated air, which is supplied to the space 14 by a conduit 70 in communication with a pump 72 suitably driven by motor means 74. Pressurized air at an elevated temperature is pumped through the conduit 70 into the space 14, through the chambers 34 as they rotate through the space 14, and through the plate 28 to a discharge conduit 76. At least some of the heated air, or what has actually become the flue gas upon passing through the catalyst bed 52, is also conducted through the heat exchanger 68 to aid in preheating the inflowing hydrocarbon gas entering the space 17. A portion of the flue gas is also conducted through a second heat exchanger 80 to aid in preheating the air flowing through the conduit 70. Additional heat exchanging apparatus which may be required for preheating the hydrocarbon gas and air flowing through the apparatus 10 has been been omitted from the diagram of FIG. 3.

Since the supports 20 and 22 form part of the partition between the flow passages or spaces 14 and 17, and since the drum 24 must rotate through the respective flow passages, there is preferably a clearance space between the supports 20 and 22 and the top and bottom surfaces of the drum 24. These clearance spaces normally permit some leakage flow of gas from one of the spaces 14 or 17 to the other space. Taking into consideration the flow rates of hydrocarbon gas and oxygen containing gas flowing into the respective spaces 17 and 14, one desirable way to minimize leakage from one space to the other through the clearance space between the drum 24 and the support 20 is to control the pressures in the spaces 17 and 14 upstream of the drum 24 to be substantially equal. In this respect, a pressure differential control device, generally designated by the numeral 84, is operable to sense the fluid pressure in the spaces 17 and 14 and, in particular, in the flow passage portions 86 and 88 which are defined within the duct 12 as those portions of the spaces 17 and 14 between the respective conduits 60 and 70 and the rotating drum 24.

By maintaining the gas pressures in the passages 86 and 88 substantially equal, there is essentially no leakage of gas across the partition 16 at the clearance space formed between the drum 24 and the support 20. Accordingly, the control device 84 may be set to maintain the pressures in the passages 86 and 88 equal by controlling the displacement of the pumps 64 and 72 through control of motor speed of the motor means 66 and 74, for example, or through suitable capacity control means built into or connected to the respective pumps 64 and 72. The differential pressure controller 84 might be of a type such as a type 210-62 manufactured by Paine Corporation of Seattle, Wash. which would be operable to control the speed of the motors 66 and 64 to maintain the aforementioned gas pressures substantially equal in the passage portions 86 and 88.

If the gas pressures in the passage portions 86 and 88 are maintained substantially equal and constant, an unequal pressure drop occurs as the gases flow through the chambers 34 into the passage portions 90 and 92, respectively. For example, due to different gas feed rates in terms of mass flow per unit time of a hydrocarbon gas, such as methane, and a gas, such as air, in order to maintain a suitable reaction to partially oxidize the methane, and due to the difference in viscosity of methane and air, unequal gas pressure losses will occur across the moving catalyst bed supported by the drum 24. In the example given hereinbelow, methane gas exiting the chambers 34 through the foraminous plate 28, for an inlet pressure in the passage portion 86 of 30.0 psia will decrease to 28.66 psia in the passage portion 90 while air exiting the rotating catalyst bed drum 24 into the passage 92 will be at a pressure of 28.13 psia for an inlet pressure maintained in the passage portion 88 of 30.0 psia. Accordingly, lower pressure in the passage 92 normally would result in the flow of hydrocarbon gas from the passage 90 to the passage 92 through the space formed between the bottom surface 35 of the plate 28, FIG. 4, and an opposed facing surface 23 of the support 22.

In accordance with the present invention, this leakage flow is substantially eliminated by providing the support 22, at least in part, as a generally hollow rectangular conduit, as illustrated in part in FIG. 4. The support 22 includes the upward facing surface 23 and defines an interior manifold space 25 which is in communication with the heated air or flue gas which has passed through the drum 24 and whose pressure is raised to at least the pressure of the gas in the passage 90 by a suitable pump 96, FIG. 3. The pump 96 may be driven by a suitable controllable prime mover 98 which is controlled by a controller device 100. The pressure in the passage 90 is sensed by the controller device 100 to control the pumping of gas from the conduit 76 by way of a suitable conduit 102 in communication with the interior space 25 formed in the support 22. Suitable air discharge orifices 103 are formed spaced apart along the support 22 and open into the space 25 from the surface 23 for discharging pressure air toward the bottom surface 35 of the plate 28. The controller device 100 may be of a type commercially available, such as a type also manufactured by Paine Corporation of Seattle, Wash. The controller 100 senses the pressure in the passage portion 90 and in the space 25 and adjusts the flow rate of the pump 96 to maintain a gas pressure in the space 25 so that the gaseous fluid exiting from the ports 103 is at a pressure at least equal to the hydrocarbon gas pressure in the passage 90. The controller device 100 may regulate the pressure in passage 25 through a suitable pressure regulator valve, not shown. In this way, leakage flow of hydrocarbon gas from the passage 90 into the passage 92 is substantially precluded. Moreover, by withdrawing gas from the regenerator gas flow path downstream of the drum 24, the oxygen content of the gas, such as air, is reduced and any leakage of gas flowing from the orifices 103 into the passage portion 90 is advantageously that of a gas with reduced oxygen content.

An example of conversion of a hydrocarbon gas, such as methane, to a higher hydrocarbon composition utilizing the system of the present invention is specified below assuming the following parameters. On the basis of a drum 24 having a diameter of approximately 36.0 feet, feed rates for a hydrocarbon gas such as methane, and air from an ambient source as specified in Table I, and a catalyst of a commercial type as described above, having a density of 50 lbs. per cubic foot, the catalyst bed area and height are calculated assuming the following given conditions: A weight hourly space velocity (WHSV) for methane of 0.60 and for air of 1.0 as indicated in the tabulation below. It is also assumed that the gas pressures entering the passage portions 86 and 88 are maintained at 30.0 psia, the temperature of the methane gas entering the passage portion 86 is about 1600° F. and the temperature of air entering the regenerator passage portion 88 is also approximately 1600° F.

TABLE I

|  | Methane | Air |
| --- | --- | --- |
| Feed Rate | 98,125 lb./hr | 209,612 lb./hr |
| Catalyst Inventory | 163,542 lb. | 209,612 lb. |
|  | 3,270 ft$^3$ | 4,192 ft$^3$ |
| WHSV | 0.6 | 1.0 |
| Bed Area | 445.8 ft$^2$ | 571.2 ft$^2$ |
| Bed Height | 7.34 ft | 7.34 ft |
| Velocity | 2.80 ft/sec | 2.64 ft/sec |
| Viscosity | .00032 Poise | .00045 Poise |
| Pressure Gradient | 0.182 psi/ft | 0.255 psi/ft |
| Pressure Drop | 1.336 psi | 1.872 psi |

$$\text{Drum Rotation Rate} = \frac{3,775,000 \text{ lb./hr}}{373,154 \text{ lb.}} \frac{\text{(catalyst circulation)}}{\text{(total catalyst inventory)}}$$

$$= 10.1 \text{ revolutions/hour}$$

The pressure decrease across the moving bed portions formed by the drum 24 are based on the Ergun equation. The abovementioned catalyst is assumed to be provided in the form of the cylindrical particles 51 having dimensions of approximately 0.125 inches diameter by approximately 0.375 inches length and which provide a void fraction in the drum chambers 34 of about 0.35. Accordingly, with the abovementioned operating conditions, the air pressure decrease or loss through the catalyst bed exceeds the methane pressure decrease by approximately 0.536 psi. However, any leakage of hydrocarbon gas through the gas seal space formed between the surfaces 23 and 35 is minimized by the injection of air or so-called flue gas taken from the passage portion 92 and injected into the manifold space 25 to form a gas curtain or seal in the gas seal space to prevent substantial flow of hydrocarbon gas into the flue gas discharge flow path. The abovementioned drum rotation rate is based on the minimum rate required for the parameters given to provide a stoichiometric reaction. The drum 24 may be rotated at a faster rate for temperature control and to distribute reaction heat.

Those skilled in the art will appreciate that, by providing the method and system described herein, including regulation of the pressure of the gases entering the passage portions 86 and 88, that control of the pressure differential created by the gases flowing through the passages 90 and 92 may be obtained for a given flow rate of gas through the rotating catalyst bed support drum 24 and that leakage flow of gas between the passage portions 90 and 92 may thus be minimized by forming the aforedescribed gas seal. Although preferred embodiments of the present invention has been described in detail herein, those skilled in the art will recognize that various substitutions and modifications may be made to the invention without departing from the scope and spirit of the appended claims.

What I claim is:

1. A system for converting a hydrocarbon gas to a higher hydrocarbon composition by flowing the hydrocarbon gas through a moving catalyst bed to partially oxidize the hydrocarbon gas and for regenerating a catalyst in said catalyst bed by exposure to an oxygen containing gas, said system comprising:

apparatus comprising a moving catalyst bed including a rotating support drum for supporting a catalyst which is alternately regenerated by exposure to the oxygen containing gas and reduced by exposure to the hydrocarbon gas, a support member for said drum, and said drum being interposed in means forming a duct including a partition at least partially defining means forming a first flow passage for the oxygen containing gas and means forming a second flow passage for the hydrocarbon gas;

means for pumping the oxygen containing gas through said first flow passage;

means for pumping the hydrocarbon gas through said second flow passage;

means for controlling the pressure of the oxygen containing gas and the hydrocarbon gas in said first and second flow passages, respectively;

means extending along a portion of said partition and defining a seal gas passage, orifice means opening into said seal gas passage and to a space formed between said drum and said partition for injecting a seal gas into said space to minimize the flow of gas between said first and second flow passages;

a source of seal gas operable to be placed in communication with said seal gas passage; and means for sensing the pressure of the hydrocarbon gas in a portion of said second flow passage downstream of said drum in the direction of flow of the hydrocarbon gas during operation of said system and for maintaining the pressure of seal gas flowing into said space to be substantially equal to or greater than the pressure of the hydrocarbon gas in said portion of said second flow passage.

2. The system set forth in claim 1 wherein:

said support member includes said means defining said seal gas passage and said orifice means for conducting seal gas to said space formed between said support member and a surface on said drum.

3. The system set forth in claim 1 including:

pump means for providing seal gas to said seal gas passage and said pump means is connected to conduit means for conducting oxygen containing gas flowing through said duct means and for withdrawing a portion of the oxygen containing gas for use as seal gas and from a point in said first flow passage downstream of said drum in the direction of flow of the oxygen containing gas during operation of said system.

* * * * *